United States Patent
Kamei et al.

(10) Patent No.: US 10,091,992 B2
(45) Date of Patent: Oct. 9, 2018

(54) STICKING AGENT COMPOSITION FOR AGROCHEMICAL

(71) Applicant: Kao Corporation, Tokyo (JP)

(72) Inventors: Masatoshi Kamei, Wakayama (JP); Yoshinori Tamura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/107,223

(22) PCT Filed: Jan. 28, 2015

(86) PCT No.: PCT/JP2015/052312
§ 371 (c)(1),
(2) Date: Jun. 22, 2016

(87) PCT Pub. No.: WO2015/115461
PCT Pub. Date: Aug. 6, 2015

(65) Prior Publication Data
US 2017/0105410 A1    Apr. 20, 2017

(30) Foreign Application Priority Data

Jan. 31, 2014   (JP) ................................. 2014-016688

(51) Int. Cl.
*A01N 25/24* (2006.01)
*A01N 59/20* (2006.01)
*C07C 69/604* (2006.01)

(52) U.S. Cl.
CPC ............. *A01N 25/24* (2013.01); *A01N 59/20* (2013.01); *C07C 69/604* (2013.01)

(58) Field of Classification Search
CPC ....... A01N 25/24; A01N 59/20; C07C 69/604
See application file for complete search history.

(56) References Cited

U.S. PATENT DOCUMENTS

| | | | | |
|---|---|---|---|---|
| 2,980,612 | A * | 4/1961 | Potter ..................... | C10M 5/00 508/136 |
| 6,897,184 | B2 * | 5/2005 | Kurita .................... | A01N 25/22 424/405 |
| 2004/0053788 | A1 * | 3/2004 | Hayashi ................. | A01N 25/30 504/363 |
| 2009/0029862 | A1 * | 1/2009 | Yoshii .................... | A01N 25/30 504/329 |
| 2009/0081307 | A1 | 3/2009 | Tsuda | |
| 2013/0196854 | A1 | 8/2013 | Kamei et al. | |
| 2013/0323396 | A1 | 12/2013 | Norn et al. | |
| 2014/0113827 | A1 * | 4/2014 | Goyal ..................... | A01N 25/24 504/362 |

FOREIGN PATENT DOCUMENTS

| | | |
|---|---|---|
| CN | 101379974 A | 3/2009 |
| CN | 103201365 A | 7/2013 |
| CN | 103209588 A | 7/2013 |
| CN | 103380772 A | 11/2013 |
| JP | 49-34815 | 9/1974 |
| JP | 57-1587006 A | 9/1982 |
| JP | 2005-170892 A | 6/2005 |
| JP | 2007-39370 A | 2/2007 |
| JP | 2011-148756 A | 8/2011 |
| JP | 2012-72110 A | 4/2012 |
| JP | 2012-184187 A | 9/2012 |
| JP | 2013-540847 A | 11/2013 |
| WO | WO 2012/029893 A1 | 3/2012 |
| WO | WO 2012/035020 A1 | 3/2012 |

OTHER PUBLICATIONS

International Preliminary Report on Patentability and the English translation of the Written Opinion of the International Searching Authority (Forms PCT/IB/373 and PCT/ISA/237) dated Aug. 2, 2016, for International Application No. PCT/JP2015/052312.
Machine translation of JP-2005-170892-A published on Jun. 30, 2005.
Machine translation of JP-2007-39370-A published on Feb. 15, 2007.
Machine translation of JP-2011-148756-A published on Aug. 4, 2011.
Machine translation of JP-57-158706-A published on Sep. 30, 1982.
Partial machine translation of JP-49-34815-B1 published on Sep. 18, 1974.
International Search Report issued in PCT/JP2015/052312, dated Apr. 21, 2015.
Chinese Office Action issued in corresponding Chinese Application No. 201580002624.X and dated Jun. 20, 2018. English translation portion only.

* cited by examiner

*Primary Examiner* — Doan T Phan
(74) *Attorney, Agent, or Firm* — Birch, Stewart, Kolasch & Birch, LLP

(57) ABSTRACT

The present invention is a sticking agent composition for agrochemicals, which includes a specific fatty acid triglyceride having an acyl group with 8 or more and 18 or less carbon atoms, a specific fatty acid with 12 or more and 20 or less carbon atoms, a polyoxyalkylene sorbitol fatty acid ester, and water.

22 Claims, No Drawings

STICKING AGENT COMPOSITION FOR AGROCHEMICAL

FIELD OF THE INVENTION

The present invention relates to a sticking agent composition for agrochemicals, an agrochemical composition and a method for enhancing effects of an agrochemical.

BACKGROUND OF THE INVENTION

With the purpose of preventing or exterminating disease damage caused by pests, for example, plant pathogens or harmful plant insects, present on plants, producers conduct a prevention method by diluting an agrochemical formulation such as fungicides or insecticides for agriculture or horticulture with water; and spraying on plants. However, an active ingredient of an agrochemical, which is attached to a plant surface by spraying, easily runs off by rainfall or spraying of water and also is detached or fallen off by wind, thereby damaging the pest control persistence of the agrochemical. As a result, problems have occurred such as decreases in the agricultural productivity, increases in the manpower and the production cost due to further required agrochemical application, and deterioration of environment safety by excessive applications of agrochemicals or the like.

In order to overcome these problems, sticking agents for sticking an agrochemical component on a plant surface have been conventionally developed with the purpose of preventing agrochemicals from running off, or being detached or fallen off by rainfall or the like. For example, JP-A 2005-170892 discloses a chemical for agriculture or horticulture, which has a particle size of 5 to 75 μm and contains a control agent for agriculture or horticulture and edible oil and fat.

Meanwhile, with the purpose of improving the formulation stability of an agrochemical formulation, vegetable oils have been used. For example, JP-A 2007-39370 discloses an aqueous suspended agrochemical formulation with improved suspension stability of formulation, which contains a disinfecting agrochemical active ingredient, kraft lignin, and a vegetable oil or a higher fatty acid. Further, JP-A 2011-148756 discloses an emulsion for insecticidal and miticidal use, which contains insecticidal etoxazole or an insecticide, a vegetable oil and an emulsifier and has such improved stability as to prevent etoxazole from sedimenting.

SUMMARY OF THE INVENTION

The present invention relates to a sticking agent composition for agrochemicals, which contains the following components A, B and C, and water,
Component A: a fatty acid triglyceride represented by the following formula (A), $$\begin{array}{l} CH_2OR^1 \\ CHOR^2 \\ CH_2OR^3 \end{array}$$

Formula (A)

in the formula, $R^1$, $R^2$ and $R^3$ are the same or different and denote an acyl group with 8 or more and 18 or less carbon atoms, Component B: a fatty acid represented by the following formula (B), $$R^{1b}\text{—COOH}$$

Formula (B)

in the formula, $R^{1b}$ denotes an alkyl group with 11 or more and 19 or less carbon atoms or an alkenyl group with 11 or more and 19 or less carbon atoms, and
Component C: a polyoxyalkylene sorbitol fatty acid ester Further, the present invention relates to an agrochemical composition, wherein an agrochemical technical product and a sticking agent composition for agrochemicals of the present invention are formulated.

Furthermore, the present invention relates to a method for enhancing effects of an agrochemical, which includes applying an agrochemical technical product to an object together with a sticking agent composition for agrochemicals of the present invention.

Techniques of JP-A 2005-170892, JP-A 2007-39370 and JP-A 2011-148756 have not been sufficient in improving the sticking property of an agrochemical to plants or the like and could not enhance the rain proof property or the like. Further, the stability of a sticking agent composition has not been sufficient.

The present invention provides a sticking agent composition for agrochemicals having an excellent sticking property of agrochemicals and high formulation stability.

According to the present invention, a sticking agent composition for agrochemicals having an excellent sticking property of agrochemicals and high formulation stability is provided.

Sticking property of agrochemicals is a property for enabling agrochemicals such as fungicides, insecticides, herbicides and others to be adhered to an object, and the sticking agent composition for agrochemicals of the present invention is for improving such sticking property of agrochemicals. Improving the sticking property of agrochemicals prevents the agrochemicals from running off by rainfalls, etc. and being detached or fallen off, thereby maintaining the effects of the agrochemicals on objects such as plants for a long period and improving the rain proof and others.

DETAILED DESCRIPTION OF THE INVENTION

[Sticking Agent Composition for Agrochemicals]
<Component A>

The component A is a fatty acid triglyceride represented by the above-described formula (A). As the component A, one or more kinds of compounds are used. In the formula (A), from the viewpoint of the sticking property of agrochemicals and the stability of the sticking agent composition, $R^1$, $R^2$ and $R^3$ are the same or different and denote an acyl group with 8 or more and 18 or less carbon atoms, each denoting preferably an acyl group with 8 or more and 16 or less carbon atoms, more preferably an acyl group with 8 or more and 14 or less carbon atoms, further preferably an acyl group with 8 or more and 12 or less carbon atoms, and further more preferably an acyl group with 8 or more and 10 or less carbon atoms. From the viewpoint of the sticking property of agrochemicals and the stability of the sticking agent composition, $R^1$, $R^2$ and $R^3$ are each preferably a linear acyl group. Further, from the same viewpoint, $R^1$, $R^2$ and $R^3$ are each preferably a saturated acyl group.

The component A is a fatty acid triglyceride, wherein $R^1$, $R^2$ and $R^3$ in the formula (A) are the same or different and denote a linear saturated acyl group with preferably 8 or more and 18 or less carbon atoms, more preferably 8 or more and 16 or less carbon atoms, further preferably 8 or more and 14 or less carbon atoms, further more preferably 8 or more and 12 or less carbon atoms, and further more preferably 8 or more and 10 or less carbon atoms.

From the viewpoint of the sticking property of agrochemicals and the stability of the sticking agent composition, the fatty acid forming a fatty acid triglyceride of the component A is caprylic acid, capric acid, lauric acid, myristic acid, palmitic acid, stearic acid, oleic acid, linoleic acid, linolenic acid, or the like; more preferably one or more kinds of fatty acids selected from caprylic acid, capric acid, lauric acid, myristic acid and palmitic acid; further preferably one or more kinds of fatty acids selected from caprylic acid, capric acid, lauric acid and myristic acid; further more preferably one or more kinds of fatty acids selected from caprylic acid, capric acid and lauric acid; and further more preferably two or more kinds of fatty acids selected from caprylic acid, capric acid and lauric acid. Fatty acids forming the fatty acid triglyceride of the component A include preferably one or more kinds of fatty acids selected from caprylic acid, capric acid, lauric acid and myristic acid; further more preferably one or more kinds of fatty acids selected from caprylic acid, capric acid and lauric acid; and further more preferably two or more kinds of fatty acids selected from caprylic acid, capric acid and lauric acid. Two or more kinds of fatty acids may be used. Further, two or more kinds of fatty acid triglycerides having different carbon numbers may be used.

From the viewpoint of the sticking property of agrochemicals and the stability of the sticking agent composition, fatty acids forming the fatty acid triglyceride of the component A are preferably caprylic acid and capric acid; and in that case, the mass ratio of caprylic acid and capric acid is preferably 10/90 or more, more preferably 50/50 or more, further preferably 70/30 or more, and preferably 90/10 or less. Therefore, $R^1$, $R^2$ and $R^3$ in the formula (A) of the component A are the same or different and denote preferably an acyl group with 8 carbon atoms and an acyl group with 10 carbon atoms. Further, in the formula (A) of the component A, $R^1$, $R^2$ and $R^3$ are the same or different and denote preferably an acyl group selected from an acyl group with 8 carbon atoms and an acyl group with 10 carbon atoms. Furthermore, the component A is also preferably a combination of a fatty acid triglyceride, wherein $R^1$, $R^2$ and $R^3$ in the formula (A) are all an acyl group with 8 carbon atoms; a fatty acid triglyceride, wherein $R^1$, $R^2$ and $R^3$ in the formula (A) are all an acyl group with 10 carbon atoms; and a fatty acid triglyceride, wherein part of $R^1$, $R^2$ and $R^3$ in the formula (A) is an acyl group with 8 carbon atoms and the rest is an acyl group with 10 carbon atoms. Further, the component A is also preferably one or more kinds of fatty acid triglycerides selected from a fatty acid triglyceride, wherein $R^1$, $R^2$ and $R^3$ in the formula (A) are all an acyl group with 8 carbon atoms; a fatty acid triglyceride, wherein $R^1$, $R^2$ and $R^3$ in the formula (A) are all an acyl group with 10 carbon atoms; and a fatty acid triglyceride, wherein part of $R^1$, $R^2$ and $R^3$ in the formula (A) is an acyl group with 8 carbon atoms and the rest is an acyl group with 10 carbon atoms.

The fatty acid triglyceride of the component A may be a triglyceride derived from vegetable oils or animal oils, and preferably a triglyceride derived from vegetable oils from the viewpoint of its reduced burden on the environment. From the viewpoint of the sticking property of agrochemicals and the stability of the sticking agent composition, the vegetable oil is preferably palm oil, palm kernel oil, rapeseed oil, sesame oil, coconut oil, corn oil, olive oil, peanut oil, sunflower oil, soybean oil, cottonseed oil, rice oil, rice bran oil, castor oil and safflower oil; more preferably palm oil, palm kernel oil, rapeseed oil, coconut oil and rice bran oil; further preferably palm kernel oil and coconut oil; and further more preferably coconut oil. Vegetable oils or animal oils containing the component A may be used as the component A without being processed.

From the viewpoint of the sticking property of agrochemicals and the stability of the sticking agent composition, the component A is preferably one or more kinds of fatty acid triglycerides selected from the following (A1), (A2), (A3) and (A4), more preferably one or more kinds of fatty acid triglycerides selected from the following (A1), (A2) and (A3), further preferably one or more kinds of fatty acid triglycerides selected from (A1) and (A2), and further more preferably fatty acid triglycerides selected from (A1).

(A1) a fatty acid triglyceride, wherein $R^1$, $R^2$ and $R^3$ in the formula (A) are a combination of an acyl group with 8 carbon atoms and an acyl group with 10 carbon atoms, a fatty acid triglyceride, wherein $R^1$, $R^2$ and $R^3$ are in the formula (A) are an acyl group of mixed fatty acid of caprylic acid and capric acid, or a triglyceride of glycerin and mixed fatty acid of caprylic acid and capric acid;
(A2) a fatty acid triglyceride, wherein $R^1$, $R^2$ and $R^3$ in the formula (A) are each an acyl group with 8 carbon atoms;
(A3) a triglyceride derived from coconut oil; and
(A4) a triglyceride derived from palm kernel oil.

From the viewpoint of the sticking property of agrochemicals and the stability of the sticking agent composition, the sticking agent composition for agrochemicals of the present invention contains the component A in an amount of preferably 5% by mass or more, more preferably 10% by mass or more, further preferably 15% by mass or more, and further more preferably 20% by mass or more; and preferably 60% by mass or less, more preferably 50% by mass or less, further preferably 45% by mass or less, and further more preferably 40% by mass or less.

<Component B>

The component B is a fatty acid represented by the above-described formula (B). As the component B, one or more kinds of compounds are used. In the formula (B), from the viewpoint of the sticking property of agrochemicals and the stability of the sticking agent composition, $R^{1b}$ is an alkyl group with 11 or more and 19 or less carbon atoms or an alkenyl group with 11 or more and 19 or less carbon atoms. From the viewpoint of the sticking property of agrochemicals and the stability of the sticking agent composition, $R^{1b}$ is preferably a liner alkyl group or a linear alkenyl group. Further, from the viewpoint of the sticking property of agrochemicals and the stability of the sticking agent composition, $R^{1b}$ is preferably unsaturated, that is an alkenyl group. From the viewpoint of the sticking property of agrochemicals and the stability of the sticking agent composition, $R^{1b}$ is preferably an alkenyl group with 11 or more and 19 or less carbon atoms. From the viewpoint of the sticking property of agrochemicals and the stability of the sticking agent composition, the carbon number of $R^{1b}$ is preferably 13 or more and 17 or less, more preferably 15 or more and 17 or less, and further preferably 17. From the viewpoint of the sticking property of agrochemicals and the stability of the sticking agent composition, $R^{1b}$ is preferably an alkyl group with 13 or more and 17 or less carbon atoms or an alkenyl group with 13 or more and 17 or less carbon atoms, and more preferably an alkenyl group with 13 or more and 17 or less carbon atoms. From the viewpoint of the sticking property of agrochemicals and the stability of the sticking agent composition, $R^{1b}$ is preferably a linear alkyl group with 17 carbon atoms or a liner alkenyl group with 17 carbon atoms, and more preferably a linear alkenyl group with 17 carbon atoms.

From the viewpoint of the sticking property of agrochemicals and the stability of the sticking agent composition, the component B is preferably lauric acid, myristic acid, palmitic acid, stearic acid, oleic acid, linoleic acid, linolenic acid, arachidic acid, arachidonic acid or the like; more preferably one or more kinds of fatty acids selected from myristic acid, palmitic acid, stearic acid, oleic acid, linoleic acid and linolenic acid; further preferably one or more kinds of fatty acids selected from palmitic acid, stearic acid, oleic acid, linoleic acid and linolenic acid; further more preferably one or more kinds of fatty acids selected from oleic acid, linoleic acid and linolenic acid; and further more preferably oleic acid. As the component B, two or more kinds of fatty acids having different carbon numbers may be used.

From the viewpoint of the sticking property of agrochemicals and the stability of the sticking agent composition, the sticking agent composition for agrochemicals of the present invention contains the component B in an amount of preferably 0.5% by mass or more, more preferably 1% by mass or more, further preferably 2% by mass or more, further more preferably 3% by mass or more and further more preferably 4% by mass or more; and preferably 12% by mass or less, more preferably 10% by mass or less, further preferably 9% by mass or less, further more preferably 7% by mass or less.

<Component C>

The component C is a polyoxyalkylene sorbitol fatty acid ester. As the component C, one or more kinds of compounds are used.

In the component C, the addition molar number of oxyalkylene group relative to 1 mole of sorbitol is, from the viewpoint of the sticking property of agrochemicals and the stability of the sticking agent composition, preferably 10 or more, more preferably 15 or more, further preferably 20 or more, further more preferably 25 or more, further more preferably 30 or more and further more preferably 35 or more; and preferably 80 or less, more preferably 65 or less, further preferably 60 or less, further more preferably 55 or less and further more preferably 50 or less. From the viewpoint of the sticking property of agrochemicals and the stability of the sticking agent composition, the oxyalkylene group is preferably a group selected from an oxyethylene group and an oxypropylene group, and more preferably an oxyethylene group.

The carbon number of an acyl group of a fatty acid forming the component C is, from the viewpoint of the sticking property of agrochemicals and the stability of the sticking agent composition, preferably 8 or more, more preferably 12 or more, further preferably 14 or more and further more preferably 16 or more; and preferably 22 or less, more preferably 18 or less and further preferably 18. The acyl group of fatty acid forming the component C is preferably linear from the viewpoint of the sticking property of agrochemicals and the stability of the sticking agent composition. Further, the acyl group of fatty acid forming the component C is preferably unsaturated from the viewpoint of the sticking property of agrochemicals and the stability of the sticking agent composition. The fatty acid forming the component C is preferably an unsaturated fatty acid. Further, from the viewpoint of the sticking property of agrochemicals and the stability of the sticking agent composition, the acyl group of fatty acid forming the component C is preferably an acyl group of a fatty acid selected from caprylic acid, lauric acid, myristic acid, palmitic acid, stearic acid, oleic acid, linoleic acid, linolenic acid, arachidic acid, arachidonic acid and behenic acid; more preferably an acyl group of a fatty acid selected from lauric acid, myristic acid, palmitic acid, stearic acid, oleic acid, linoleic acid and linolenic acid; further preferably an acyl group of a fatty acid selected from oleic acid, linoleic acid and linolenic acid; and further more preferably an acyl group of oleic acid.

Examples of the component C include polyoxyalkylene sorbitol fatty acid esters, wherein, from the viewpoint of the sticking property of agrochemicals and the stability of the sticking agent composition, the addition molar number of oxyalkylene group relative to 1 mole of sorbitol is preferably 10 or more, more preferably 15 or more, further preferably 20 or more, further preferably 25 or more, further more preferably 30 or more and further more preferably 35 or more; and preferably 80 or less, more preferably 65 or less, further preferably 60 or less, further more preferably 55 or less and further more preferably 50 or less; the oxyalkylene group is preferably one or more kinds of groups selected an oxyethylene group and an oxypropylene group, and more preferably an oxyethylene group; the carbon number of the acyl group of fatty acid is preferably 8 or more, more preferably 12 or more, further preferably 14 or more and further more preferably 16 or more; and preferably 22 or less, more preferably 18 or less and further preferably 18; and the acyl group of fatty acid is an acyl group of an unsaturated fatty acid.

From the viewpoint of the sticking property of agrochemicals and the stability of the sticking agent composition, the number of acyl groups in the component C, that is the degree of esterification, is preferably 1 or more, more preferably 2 or more and further preferably 3 or more; and preferably 5 or less, more preferably 4 or less and further preferably 4. Examples of the component C include mono-fatty acid esters, di-fatty acid esters, tri-fatty acid esters, tetra-fatty acid esters and penta-fatty acid esters of a sorbitol alkylene oxide adduct; and, they are, from the viewpoint of the sticking property of agrochemicals and the stability of the sticking agent composition, preferably tri-fatty acid esters, tetra-fatty acid esters or penta-fatty acid esters of a sorbitol alkylene oxide adduct, more preferably tetra-fatty acid esters or penta-fatty acid esters of a sorbitol alkylene oxide adduct, and further preferably tetra-fatty acid esters of a sorbitol alkylene oxide adduct. Preferable forms of these fatty acids or alkylene oxide (oxyalkylene groups) are as described above.

From the viewpoint of the sticking property of agrochemicals and the stability of the sticking agent composition, the component C is preferably one or more kinds of polyoxyalkylene sorbitol fatty acid esters selected from the following (C1), (C2) and (C3); and more preferably one or more kinds of polyoxyalkylene sorbitol fatty acid esters selected from the following (C2). From the same viewpoint, the oxyalkylene group in (C1), (C2) and (C3) is preferably one or more kinds of groups selected from an oxyethylene group and an oxypropylene group, and more preferably an oxyethylene group.

(C1) a polyoxyalkylene sorbitol tri-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms;

(C2) a polyoxyalkylene sorbitol tetra-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms; and (C3) a polyoxyalkylene sorbitol penta-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms.

From the viewpoint of the sticking property of agrochemicals and the stability of the sticking agent composition, the component C is one or more kinds of polyoxyalkylene sorbitol fatty acid esters selected from the following (C1-1), (C2-1) and (C3-1), more preferably one or more kinds of polyoxyalkylene sorbitol fatty acid esters selected from the following (C2-1). From the same viewpoint, the oxyalkylene group in (C1-1), (C2-1) and (C3-1) is preferably one or more kinds of groups selected from an oxyethylene group and an oxypropylene group, preferably an oxyethylene group.

(C1-1) a polyoxyalkylene sorbitol tri-fatty acid ester, wherein the addition molar number of the oxyalkylene group relative to 1 mole of sorbitol is 30 or more and 60 or less, and the fatty acid forming the component C is oleic acid;

(C2-1) a polyoxyalkylene sorbitol tetra-fatty acid ester, wherein the addition molar number of the oxyalkylene group relative to 1 mole of sorbitol is 30 or more and 60 or less, and the fatty acid forming the component C is oleic acid; and (C3-1) a polyoxyalkylene sorbitol penta-fatty acid ester, wherein the addition molar number of the oxyalkylene group relative to 1 mole of sorbitol is 30 or more and 60 or less, and the fatty acid forming the component C is oleic acid.

As the component C, two or more kinds of polyoxyalkylene sorbitol fatty acid esters that differ in the addition molar number of alkylene oxide, the carbon number of fatty acids, the degree of esterification or the like may be used.

The component C can be prepared by adding a predetermined amount of alkylene oxide to sorbitol to obtain an alkylene oxide adduct of sorbitol, and then esterifying the resultant with a fatty acid. From the viewpoint of the sticking property of agrochemicals and the stability of the sticking agent composition, the alkylene oxide is preferably an alkylene oxide selected from ethylene oxide and propylene oxide, more preferably ethylene oxide.

The kind of alkylene oxide, the kind of fatty acid, the feeding amount or the like may be changed, and thereby various polyoxyalkylene sorbitol fatty acid esters as the component C can be synthesized.

From the viewpoint of the sticking property of agrochemicals and the stability of the sticking agent composition, the sticking agent composition for agrochemicals of the present invention contains the component C in an amount of preferably 1% by mass or more, more preferably 2% by mass or more, further preferably 3% by mass or more and further more preferably 4% by mass; and preferably 12% by mass or less, more preferably 10% by mass or less, further preferably 9% by mass or less and further preferably 7% by mass or less.

<Water>

The sticking agent composition for agrochemicals of the present invention contains water. As the water, tap water, distilled water, ion exchanged water or the like may be used without impairing the effects of the sticking agent composition for agrochemicals, and preferably ion exchange water is used from the viewpoint of the sticking property of agrochemicals and the stability of the sticking agent composition.

The water content of the sticking agent composition for agrochemicals of the present invention is the rest except the components A, B and C, and other components; and, from the viewpoint of the sticking property of agrochemicals and the stability of the sticking agent composition, it is preferably 16% by mass or more, more preferably 20% by mass or more, further preferably 30% or more, further more preferably 40% by more, further more preferably 50% by mass or more and further more preferably 55% by mass or more; and preferably 93.5% by mass or less, more preferably 90% by mass or less, further preferably 85% by mass or less, further more preferably 80% by mass or less, further more preferably 70% by mass or less and further more preferably 62% by mass or less.

<Other Components, Forms, Compositions or the Like>

The sticking agent composition for agrochemicals of the present invention may contain compounds other than the components A, B and C, and water, such as compounds used as oil or a surfactant.

The sticking agent composition of the present invention is a liquid composition containing water. In the sticking agent composition for agrochemicals of the present invention, the total content of the components A, B and C is, from the viewpoint of the stability of the sticking agent composition and the economical viewpoint, preferably 10% by mass of more, more preferably 15% by mass or more, further preferably 20% by mass or more, further more preferably 30% by mass or more and further more preferably 38% by mass or more; and preferably 80% by mass or less, more preferably 70% by mass or less, further preferably 60% by mass or less, further more preferably 50% by mass or less and further more preferably 45% by mass or less.

From the viewpoint of the sticking property of agrochemicals and the stability of the sticking agent composition, the sticking agent composition for agrochemicals of the present invention has a pH at 25° C. of preferably 2.0 or more, more preferably 3.0 or more, further preferably 3.5 or more and further more preferably 4.5 or more; and preferably 11 or less, more preferably 9 or less, further preferably 7 or less, further more preferably 6.5 or less and further more preferably 5.5 or less.

From the viewpoint of the sticking property of agrochemicals and the stability of the sticking agent composition, the sticking agent composition for agrochemicals of the present invention has a viscosity at 25° C. of preferably 1.0 mPa·s or more, more preferably 2.0 mPa·s or more, further preferably 3.0 mPa·s or more, further more preferably 4.0 mPa·s or more and further more preferably 5.0 mPa·s or more; and preferably 10000 mPa·s or less, more preferably 1000 mPa·s or less, further preferably 100 mPa·s or less, further more preferably 50 mPa·s or less, further more preferably 30 mPa·s or less, further more preferably 20 mPa·s or less, further more preferably 15 mPa·s or less and further more preferably 13 mPa·s or less.

The viscosity measurement is performed on a composition at 25° C. by use of a Brookfield viscosity meter. Regarding the measurement conditions, a rotor and a number of rotations suitable for measuring a viscosity in the above range may be selected. For example, when the measurement is performed by a TVB-10M type viscometer manufactured by Toki Sangyo Co., Ltd., the rotor to be used is No. 20 and the rotation speed is 60 rpm.

In the sticking agent composition for agrochemicals of the present invention, from the viewpoint of the sticking property of agrochemicals and the stability of the sticking agent composition, the mass ratio of the component A to the component B, component A/component B, is preferably 1 or more, more preferably 2 or more, further preferably 3 or more and further more preferably 4 or more; and preferably 30 or less, more preferably 20 or less, further preferably 10 or less and further more preferably 7 or less.

In the sticking agent composition for agrochemicals of the present invention, from the viewpoint of the sticking property of agrochemicals and the stability of the sticking agent composition, the mass ratio of the component A to the component C, component A/component C, is preferably 1 or more, more preferably 2 or more, further preferably 3 or more, further more preferably 4 or more and further more preferably 4.5 or more; and preferably 30 or less, more preferably 20 or less, further preferably 10 or less, further more preferably 8 or less, further more preferably 7 or less and further more preferably 6 or less.

In the sticking agent composition for agrochemicals of the present invention, from the viewpoint of the sticking property of agrochemicals and the stability of the sticking agent composition, the mass ratio of the component B to the component C, component B/component C, is preferably 0.1 or more, more preferably 0.2 or more, further preferably 0.5 or more, further more preferably 0.8 or more and further more preferably 1.0 or more; and preferably 5 or less, more preferably 3 or less, further preferably 2 or less and further more preferably 1.5 or less.

In the sticking agent composition for agrochemicals of the present invention, from the viewpoint of the sticking property of agrochemicals and the stability of the sticking agent composition, the mass ratio of the total of the components A and B to the component C, (component A+component B)/component C, is preferably 1 or more, more preferably 3 or more, further preferably 4 or more, further more preferably 6 or more and further more preferably 6.5 or more; and preferably 30 or less, more preferably 15 or less, further preferably 10 or less, further preferably 8 or less and further preferably 7.5 or less.

In the sticking agent composition for agrochemicals of the present invention, from the viewpoint of the sticking property of agrochemicals and the stability of the sticking agent composition, the mass ratio of the component A to the total of the components B and C, component A/(component B+component C), is preferably 0.5 or more, more preferably 1.0 or more, further preferably 1.5 or more, further more preferably 2.0 or more and further more preferably 2.4 or more; and preferably 6.0 or less, more preferably 5.0 or less, further preferably 4.5 or less, further more preferably 3.5 or less and further more preferably 3.0 or less.

The sticking agent composition for agrochemicals of the present invention can be prepared by, for example, mixing the components A, B and C, and gradually adding a predetermined amount of water while stirring. Further, the order of feeding each component may be varied. The temperature during the preparation is, from the viewpoint of the sticking property of agrochemicals and the stability of the sticking agent composition, preferably 30 C.° or more and 100° C. or less, more preferably 40° C. or more and 90° C. or less, and further preferably 50° C. or more and 80° C. or less.

The present invention provides a method for producing a sticking agent composition for agrochemicals, which includes mixing the components A, B and C, and water. According to this production method, the sticking agent composition for agrochemicals of the present invention is produced. In the method for producing a sticking agent composition for agrochemicals of the present invention, it is preferred to mix the components A, B and C at preferably 30° C. or higher, more preferably 40° C. or higher and further preferably 50° C. or higher; and preferably 100° C. or lower, more preferably 90° C. or lower and further preferably 80° C. or lower; and mix the obtained mixture with water having a temperature of preferably 30° C. or higher, more preferably 40° C. or higher and further preferably 50° C. or higher; and preferably 100° C. or lower, more preferably 90° C. or lower and further preferably 80° C. or lower.

The matters mentioned for the sticking agent composition for agrochemicals of the present invention can be appropriately applied to the method for producing a sticking agent composition for agrochemicals of the present invention.

The sticking agent composition for agrochemicals is mixed with an agrochemical technical product such as insecticides, fungicides, herbicides and others, diluted with water to provide a predetermined concentration, and applied to stems, leaves and others of plants. When the sticking agent composition for agrochemicals of the present invention and the agrochemical technical product (agrochemical formulation) are mixed and diluted with water, fine emulsified matters where the components A and B are mixed, are emulsified and dispersed in water by the component C. Then, it is believed that calcium ions or the like present in water used for dilution or blended in the agrochemical (agrochemical formulation) are bonded to the component B in the fine emulsified matters and a strong coating of a composite of the fine emulsified matter is formed, thereby exhibiting non-conventional sticking property of the agrochemical. Lacking of any one of the components A, B and C deteriorates the effect of improving the sticking property of an agrochemical.

The present invention provides a sticking agent composition for agrochemicals containing the following components A, B and C, and water. The above-mentioned matters can be appropriately applied to this sticking agent composition for agrochemicals.

Component A: a fatty acid triglyceride represented by the following formula (A),

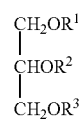

Formula (A)

in the formula, $R^2$, $R^2$ and $R^3$ are the same or different and denote an acyl group with 8 or more and 18 or less carbon atoms, preferably an acyl group with 8 or more and 12 or less carbon atoms, Component B: a fatty acid represented by the following formula (B),

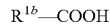

Formula (B)

in the formula, $R^{1b}$ denotes an alkyl group with 11 or more and 19 or less carbon atoms or an alkenyl group with 11 or more and 19 or less carbon atoms, preferably an alkyl group with 13 or more and 17 or less carbon atoms or an alkenyl group with 13 or more and 17 or less carbon atoms, and Component C: one or more kinds of polyoxyalkylene sorbitol fatty acid esters selected from the following (C1), (C2) and (C3), (C1) polyoxyalkylene sorbitol tri-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms;

(C2) polyoxyalkylene sorbitol tetra-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms; and
(C3) polyoxyalkylene sorbitol penta-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms.

Further, the present invention provides a sticking agent composition for agrochemicals, which contains the following components A, B and C, and water. The above-mentioned matters can be appropriately applied to this sticking agent composition for agrochemicals.

Component A: a fatty acid triglyceride represented by the following formula (A),

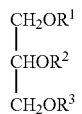

Formula (A)

in the formula, $R^2$, $R^2$ and $R^3$ are the same or different and denote an acyl group with 8 or more and 18 or less carbon atoms, preferably an acyl group with 8 or more and 12 or less carbon atoms, Component B: a fatty acid represented by the following formula (B),

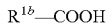

Formula (B)

in the formula, $R^{1b}$ denotes an alkyl group with 11 or more and 19 or less carbon atoms or an alkenyl group with 11 or more and 19 or less carbon atoms, preferably an alkyl group with 13 or more and 17 or less carbon atoms or an alkenyl group with 13 or more and 17 or less carbon atoms, and
Component C: one or more kinds of polyoxyalkylene sorbitol fatty acid esters selected from the following (C1-1), (C2-1) and (C3-1),
(C1-1) polyoxyalkylene sorbitol tri-fatty acid ester, wherein the addition molar number of the oxyalkylene group relative to 1 mole of sorbitol is 30 or more and 60 or less, and the fatty acid forming the component C is oleic acid;
(C2-1) polyoxyalkylene sorbitol tetra-fatty acid ester, wherein the addition molar number of the oxyalkylene group relative to 1 mole of sorbitol is 30 or more and 60 or less, and the fatty acid forming the component C is oleic acid; and
(C3-1) polyoxyalkylene sorbitol penta-fatty acid ester, wherein the addition molar number of the oxyalkylene group relative to 1 mole of sorbitol is 30 or more and 60 or less, and the fatty acid forming the component C is oleic acid.

[Agrochemical Composition]

An agrochemical composition of the present invention contains an agrochemical technical product and a sticking agent composition for agrochemicals, which are blended with each other.

Examples of agrochemical technical products used for the agrochemical composition of the present invention includes any of agrochemical technical products selected from individual active ingredients of fungicides, insecticides, miticides and herbicides. The agrochemical technical product used herein refers to compounds as active ingredients of agrochemicals.

Examples the agrochemical technical product used for the agrochemical composition of the present invention include, but not limited to, those described in, for example, NOYAKU HANDOBUKKU 2011 NENDO-BAN (Agrochemical Handbook 2011 edition) (issued by Japan Plant Protection Association, Feb. 25, 2011). Further, the sticking agent composition for agrochemicals of the present invention and agrochemical compositions containing it do not cause chemical injury on various crops and they can be used safely.

Examples of the fungicide include those listed in, for example, International Publication No. 2012/029893. From the viewpoint of the sticking property of agrochemicals, used as fungicides are preferably basic copper sulfate, an organocopper compound (Oxine-copper) and cupric hydroxide, more preferably basic copper sulfate.

Examples of the insecticide include those listed in, for example, International Publication No. 2012/029893. From the viewpoint of the sticking property of agrochemicals, used as insecticides are preferably permethrin, DDVP (dimethyl 2,2-dichlorovinylphosphate), methomyl (S-methyl N-[(methylcarbamoyl)oxy]thioacetimide), and acephate (O,S-dimethyl N-acetyl phosphoramidothioate), more preferably acephate.

Examples of the miticide include those listed in, for example, International Publication No. 2012/029893. From the viewpoint of the sticking property of agrochemicals, used as miticides are preferably phenisobromolate (4,4'-dibromobenzilic acid isopropyl ester), amitraz(3-methyl-1,5-bis(2,4-xylyl)-1,3,5-trazapenta-1,4-diene) and fenpyroximate (tert-butyl=(E)-α-(1,3-dimethyl-5-phenoxypyrazol-4-ylmethyleneaminooxy-p-toluate).

Examples of the herbicides include those listed in, for example, International Publication No. 2012/029893. From the viewpoint of the sticking property of agrochemicals, used as herbicides are preferably DBN (2,6-dichlorobenzonitrile), DCMU (3-(3,4-dichlorophenyl)-1,1-dimethylurea), paraquat (1,1'-dimethyl-4,4'-bipyridinium dichloride), diquat (6,7-dihydrodipyrido[1,2-a:2',1'c]pyrazinediium dibromide) and glyphosate (N-(phosphonomethyl)glycine and salts thereof), preferably glyphosate.

As for an agrochemical composition of the present invention, the formulation concentration of an agrochemical technical product in the agrochemical composition is, from the viewpoint of exhibiting the effect of the agrochemical technical product, preferably 10 ppm or more, more preferably 100 ppm or more and further preferably 500 ppm or more; and preferably 200000 ppm or less, more preferably 50000 ppm or less and further preferably 30000 ppm or less.

In the agrochemical composition of the present invention, the formulation concentration of the sticking agent composition for agrochemicals of the present invention is, from the viewpoint of preventing droplets adhered to plants or harmful insects from dripping off to increase a deposit amount and enhancing the sticking of the agrochemical technical product, preferably 100 ppm or more, more preferably 500 ppm or more and further preferably 1000 ppm or more; and preferably 20000 ppm or less, more preferably 10000 ppm or less and further preferably 4000 ppm or less.

The formulation concentration of the component A in the agrochemical composition of the present invention is, from the viewpoint of enhancing the sticking of the agrochemical technical product, preferably 50 ppm or more, more preferably 150 ppm or more, further preferably 200 ppm or more and further more preferably 300 ppm or more; and preferably 15000 ppm or less, more preferably 5000 ppm or less, further preferably 1000 ppm or less and further more preferably 800 ppm or less.

The formulation concentration of the component B in the agrochemical composition of the present invention is, from the viewpoint of enhancing the sticking of the agrochemical technical product, preferably 15 ppm or more, more preferably 20 ppm or more, further preferably 50 ppm or more and further more preferably 80 ppm or more; and preferably 2000 ppm or less, more preferably 1000 ppm or less, further preferably 500 ppm or less, further more preferably 300 ppm or less, further more preferably 180 ppm or less and further more preferably 150 ppm or less.

The formulation concentration of the component C in the agrochemical composition of the present invention is, from the viewpoint of enhancing the sticking of the agrochemical technical product, preferably 15 ppm or more, more preferably 50 ppm or more, further preferably 60 ppm or more and further preferably 80 ppm or more; and preferably 2000 ppm or less, more preferably 1000 ppm or less, further preferably 500 ppm or less, further more preferably 300 ppm or less, further preferably 180 ppm or less and further more preferably 150 ppm or less.

Further, the agrochemical composition of the present invention may be in any formulation form of emulsion, liquid formulation, wettable powder, granule, flowable formulation and the like, and any formulation form is applicable. Therefore, such formulation form may contain other additives therefor, such as an emulsifier, a solvent, a dispersant, a carrier or the like. Methods of using the sticking agent composition for agrochemicals of the present invention include, for example, a method of using an agrochemical composition in the above-described various formulation forms formulated with the sticking agent composition for agrochemicals, and a method of using the sticking agent composition for agrochemicals at the time of diluted use of an agrochemical (not containing the sticking agent composition for agrochemicals of the present invention), and either of the methods can provide an excellent sticking effect of an agrochemical, which is a purpose of the present invention.

If necessary, a chelating agent, a pH adjusting agent, an inorganic salt, and/or a thickener may be added to the formulation of the agrochemical composition of the present invention.

Further, the sticking agent composition for agrochemicals of the present invention improves the sticking property of agrochemicals, and as a result, effects of the agrochemicals can be enhanced. Thus, there is provided a method for enhancing effects of an agrochemical, which includes applying to an object an agrochemical technical product selected from agrochemical technical products such as fungicides, insecticides, miticides and herbicides together with the above-described sticking agent composition for agrochemicals of the present invention.

In addition, as the sticking agent composition for agrochemicals of the present invention improves the rain proof of agrochemicals, there is provided a method for enhancing the rain proof of an agrochemical, which includes applying to an object an agrochemical technical product selected from agrochemical technical products such as fungicides, insecticides, miticides and herbicides together with the above-described sticking agent composition for agrochemicals of the present invention. The above-described method for enhancing effects of an agrochemical of the present invention may be a method for enhancing effects of an agrochemical by improving the rain proof of the agrochemical.

Furthermore, as the sticking agent composition for agrochemicals of the present invention improves the sticking property of an agrochemical, there is provided a method for improving the sticking property of an agrochemical, which includes applying to an object an agrochemical technical product selected from agrochemical technical products such as fungicides, insecticides, miticides and herbicides together with the above-described sticking agent composition for agrochemicals of the present invention. The above-described method for enhancing effects of an agrochemical of the present invention may be a method for enhancing effects of an agrochemical by improving the sticking property of the agrochemical.

As objects of an agrochemical technical product in the present invention, fungi, disease and pest (insects), mites and weeds (plants that are not crops) are objects of fungicides, insecticides, miticides and herbicides, respectively, and a plurality of them may be objects at the same time. Further, the method for enhancing effects of an agrochemical can be implemented as a method for applying an agrochemical composition of the present invention to an object selected from weeds, mites, disease and pest and fungi, for example, a method for spraying on a cultivation area of crops.

The present invention provides a method for producing an agrochemical composition, wherein an agrochemical technical product, components A, B and C, and water are mixed. The agrochemical technical product, and the components A, B and C are used so as to have the above-described formulation concentrations in the agrochemical composition. The matters mentioned on the sticking agent composition for agrochemicals of the present invention and the agrochemical composition of the present invention can be appropriately applied to the method for producing an agrochemical composition of the present invention.

Examples of the Present Invention

Hereinafter, examples of the present invention are exemplified. The matters mentioned on the sticking agent composition for agrochemicals, the agrochemical composition and the method for enhancing effects of agrochemicals according to the present invention can be appropriately applied to these examples.

<1> A sticking agent composition for agrochemicals, containing the following components A, B and C, and water, Component A: a fatty acid triglyceride represented by the following formula (A),

Formula (A)

in the formula, $R^2$, $R^2$ and $R^3$ are the same or different and denote an acyl group with 8 or more and 18 or less carbon atoms, Component B: a fatty acid represented by the following formula (B),

Formula (B)

in the formula, $R^{1b}$ denotes an alkyl group with 11 or more and 19 or less carbon atoms or an alkenyl group with 11 or more and 19 or less carbon atoms, and Component C: a polyoxyalkylene sorbitol fatty acid ester
<2> The sticking agent composition for agrochemicals described in the above <1>, wherein the component A is a fatty acid triglyceride, in which $R^1$, $R^2$ and $R^3$ in the formula (A) are each an acyl group with 8 or more and 16 or less carbon atoms, preferably an acyl group with 8 or more and 14 or less carbon atoms, more preferably an acyl group with 8 or more and 12 or less carbon atoms, and further preferably an acyl group with 8 or more and 10 or less carbon atoms.
<3> The sticking agent composition for agrochemicals described in the above <1> or <2>, wherein the component A is a fatty acid triglyceride, in which $R^1$, $R^2$ and $R^3$ in the formula (A) are each a linear acyl group.
<4> The sticking agent composition for agrochemicals described in any one of the above <1> to <3>, wherein the component A is a fatty acid triglyceride, in which $R^1$, $R^2$ and $R^3$ in the formula (A) are each a saturated acyl group.
<5> The sticking agent composition for agrochemicals described in any one of the above <1> to <4>, wherein a fatty acid forming the fatty acid triglyceride of the component A is one or more kinds of fatty acids selected from caprylic acid, capric acid, lauric acid, myristic acid, palmitic acid, stearic acid, oleic acid, linoleic acid and linolenic acid; preferably one or more kinds of fatty acids selected from caprylic acid, capric acid, lauric acid, myristic acid and palmitic acid; more preferably one or more kinds of fatty acids selected from caprylic acid, capric acid, lauric acid and myristic acid; further preferably one or more kinds of fatty acids selected from caprylic acid, capric acid and lauric acid; and further more preferably two or more kinds of fatty acids selected from caprylic acid, capric acid and lauric acid.
<6> The sticking agent composition for agrochemicals described in any one of the above <1> to <5>, wherein the fatty acid triglyceride of the component A is a triglyceride derived from a vegetable oil, preferably a triglyceride derived from an oil selected from palm oil, palm kernel oil, rapeseed oil, sesame oil, coconut oil, corn oil, olive oil, peanut oil, sunflower oil, soybean oil, cottonseed oil, rice oil, rice bran oil, castor oil and safflower oil; more preferably a triglyceride derived from an oil selected from palm oil, palm kernel oil, rapeseed oil, coconut oil and rice bran oil; further preferably a triglyceride derived from an oil selected from palm kernel oil and coconut oil; and further more preferably a triglyceride derived from coconut oil.
<7> The sticking agent composition for agrochemicals described in any one of the above <1> to <6>, wherein the component A is one or more kinds of fatty acid triglycerides selected from the following (A1), (A2), (A3) and (A4), preferably one or more kinds of fatty acid triglycerides selected from (A1), (A2) and (A3), more preferably one or more kinds of fatty acid triglycerides selected from (A1) and (A2), further preferably one or more kinds of fatty acid triglycerides selected from (A1),
(A1) a fatty acid triglyceride, wherein $R^1$, $R^2$ and $R^3$ in the formula (A) are a combination of an acyl group with 8 carbon atoms and an acyl group with 10 carbon atoms, a fatty acid triglyceride, wherein $R^1$, $R^2$ and $R^3$ in the formula (A) are an acyl group of mixed fatty acid of caprylic acid and capric acid, or a triglyceride of glycerin and mixed fatty acid of caprylic acid and capric acid;
(A2) a fatty acid triglyceride, wherein $R^1$, $R^2$ and $R^3$ in the formula (A) are each an acyl group with 8 carbon atoms;
(A3) a triglyceride derived from coconut oil; and
(A4) a triglyceride derived from palm kernel oil.
<8> The sticking agent composition for agrochemicals described in any one of the above <1> to <6>, wherein fatty acids forming the fatty acid triglyceride of the component A are caprylic acid and capric acid, a mass ratio of caprylic acid and capric acid is preferably 10/90 or more, more preferably 50/50 or more, further preferably 70/30 or more, and preferably 90/10 or less.
<9> The sticking agent composition for agrochemicals described in any one of the above <1> to <8>, wherein the component A is present in an amount of preferably 5% by mass or more, more preferably 10% by mass or more, further preferably 15% by mass or more, and further more preferably 20% by mass or more; and preferably 60% by mass or less, more preferably 50% by mass or less, further preferably 45% by mass or less and further more preferably 40% by mass or less.
<10> The sticking agent composition for agrochemicals described in any one of the above <1> to <9>, wherein the component B is a fatty acid, in which $R^{1b}$ in the formula (B) is an alkyl group or alkenyl group having a carbon number of 13 or more and 17 or less, preferably 15 or more and 17 or less and more preferably 17.
<11> The sticking agent composition for agrochemicals described in any one of the above <1> to <10>, wherein the component B is a fatty acid, in which $R^{1b}$ in the formula (B) is a liner alkyl group or a linear alkenyl group.
<12> The sticking agent composition for agrochemicals described in any one of the above <1> to <11>, wherein the component B is a fatty acid, in which $R^{1b}$ in the formula (B) is an alkenyl group.
<13> The sticking agent composition for agrochemicals described in any one of the above <1> to <12>, wherein the component B is a fatty acid, in which $R^{1b}$ in the formula (B) is a linear alkyl group with 17 carbon atoms or a linear alkenyl group with 17 carbon atoms, further more preferably a linear alkenyl group with 17 carbon atoms.
<14> The sticking agent composition for agrochemicals described in any one of the above <1> to <13>, wherein the component B is one or more kinds of fatty acids selected from lauric acid, myristic acid, palmitic acid, stearic acid, oleic acid, linoleic acid, linolenic acid, arachidic acid and arachidonic acid; preferably one or more kinds of fatty acids selected from myristic acid, palmitic acid, stearic acid, oleic acid, linoleic acid and linolenic acid; more preferably one or more kinds of fatty acids selected from palmitic acid, stearic acid, oleic acid, linoleic acid and linolenic acid; further preferably one or more kinds of fatty acids selected from oleic acid, linoleic acid and linolenic acid; and further more preferably oleic acid.
<15> The sticking agent composition for agrochemicals described in any one of the above <1> to <14>, wherein the component B is present in an amount of preferably 0.5% by mass or more, more preferably 1% by mass or more, further preferably 2% by mass or more, further more preferably 3% by mass or more and further more preferably 4% by mass or more; and preferably 12% by mass or less, more preferably 10% by mass or less, further preferably 9% by mass or less, and further more preferably 7% by mass or less.
<16> The sticking agent composition for agrochemicals described in any one of the above <1> to <15>, wherein an addition molar number of oxyalkylene group of the component C relative to 1 mole of sorbitol is preferably 10 or more, more preferably 15 or more, further preferably 20 or more, further more preferably 25 or more, further more preferably 30 or more and further more preferably 35 or more; and preferably 80 or less, more preferably 65 or less, further preferably 60 or less, further more preferably 55 or less and further more preferably 50 or less.
<17> The sticking agent composition for agrochemicals described in any one of the above <1> to <16>, wherein the acyl group of the fatty acid forming the component C has a carbon number of preferably 8 or more, more preferably 12 or more, further preferably 14 or more and further more preferably 16 or more; and preferably 22 or less, more preferably 18 or less and further preferably 18.

<18> The sticking agent composition for agrochemicals described in any one of the above <1> to <17>, wherein the acyl group of the fatty acid forming the component C is an unsaturated acyl group.

<19> The sticking agent composition for agrochemicals described in any one of the above <1> to <17>, wherein the acyl group of the fatty acid forming the component C is preferably an acyl group of a fatty acid selected from caprylic acid, lauric acid, myristic acid, palmitic acid, stearic acid, oleic acid, linoleic acid, linolenic acid, arachidic acid, arachidonic acid and behenic acid; more preferably an acyl group of a fatty acid selected from lauric acid, myristic acid, palmitic acid, stearic acid, oleic acid, linoleic acid and linolenic acid; further preferably an acyl group of a fatty acid selected from oleic acid, linoleic acid and linolenic acid; and further more preferably an acyl group of oleic acid.

<20> The sticking agent composition for agrochemicals described in any one of the above <1> to <19>, wherein the acyl group of the fatty acid forming the component C is a linear acyl group.

<21> The sticking agent composition for agrochemicals described in any one of the above <1> to <20>, wherein a number of acyl groups in the component C, that is the degree of esterification, is preferably 1 or more, more preferably 2 or more and further preferably 3 or more; and preferably 5 or less, more preferably 4 or less and further preferably 4.

<22> The sticking agent composition for agrochemicals described in any one of the above <1> to <21>, wherein the component C is a mono-fatty acid ester, di-fatty acid ester, tri-fatty acid ester, tetra-fatty acid ester or penta-fatty acid ester of a sorbitol alkylene oxide adduct, preferably a tri-fatty acid ester, tetra-fatty acid ester or penta-fatty acid ester of a sorbitol alkylene oxide adduct; more preferably a tetra-fatty acid ester or penta-fatty acid ester of a sorbitol alkylene oxide adduct; and further preferably a tetra-fatty acid ester of a sorbitol alkylene oxide adduct.

<23> The sticking agent composition for agrochemicals described in any one of the above <1> to <22>, wherein the component C is one or more kinds of polyoxyalkylene sorbitol fatty acid esters selected from the following (C1), (C2) and (C3); preferably one or more kinds of polyoxyalkylene sorbitol fatty acid esters selected from the following (C1), (C2) and (C3), an oxyalkylene group in (C1), (C2) and (C3) being one or more kinds of groups selected from an oxyethylene group and an oxypropylene group; and more preferably one or more kinds of polyoxyalkylene sorbitol fatty acid esters selected from the following (C1), (C2) and (C3), an oxyalkylene group in (C1), (C2) and (C3) being an oxyethylene group, (C1) a polyoxyalkylene sorbitol tri-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms;

(C2) a polyoxyalkylene sorbitol tetra-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms; and (C3) a polyoxyalkylene sorbitol penta-fatty acid ester, wherein the addition molar number of the oxyalkylene group relative to 1 mole of sorbitol is 15 or more and 65 or less, and the fatty acid forming the component C is an unsaturated fatty acid with 14 or more and 22 or less carbon atoms, preferably an unsaturated fatty acid with 18 carbon atoms.

<24> The sticking agent composition for agrochemicals described in any one of the above <1> to <23>, wherein the component C is one or more kinds of polyoxyalkylene sorbitol fatty acid esters selected from the following (C1-1), (C2-1) and (C3-1); preferably one or more kinds of polyoxyalkylene sorbitol fatty acid esters selected from the following (C1-1), (C2-1) and (C3-1), an oxyalkylene group in (C1-1), (C2-1) and (C3-1) being one or more kinds of groups selected from an oxyethylene group and an oxypropylene group; and more preferably one or more kinds of polyoxyalkylene sorbitol fatty acid esters selected from the following (C1-1), (C2-1) and (C3-1), an oxyalkylene group in (C1-1), (C2-1) and (C3-1) being an oxyethylene group, (C1-1) a polyoxyalkylene sorbitol tri-fatty acid ester, wherein the addition molar number of the oxyalkylene group relative to 1 mole of sorbitol is 30 or more and 60 or less, and the fatty acid forming the component C is oleic acid;

(C2-1) a polyoxyalkylene sorbitol tetra-fatty acid ester, wherein the addition molar number of the oxyalkylene group relative to 1 mole of sorbitol is 30 or more and 60 or less, and the fatty acid forming the component C is oleic acid; and (C3-1) a polyoxyalkylene sorbitol penta-fatty acid ester, wherein the addition molar number of the oxyalkylene group relative to 1 mole of sorbitol is 30 or more and 60 or less, and the fatty acid forming the component C is oleic acid.

<25> The sticking agent composition for agrochemicals described in any one of the above <1> to <24>, wherein the component C is a polyoxyalkylene sorbitol fatty acid ester prepared by adding, to sorbitol, alkylene oxide, preferably alkylene oxide selected from ethylene oxide and propylene oxide, more preferably ethylene oxide to obtain an alkylene oxide adduct of sorbitol; and esterifying the adduct with a fatty acid.

<26> The sticking agent composition for agrochemicals described in any one of the above <1> to <25>, wherein the component C is a polyoxyalkylene sorbitol fatty acid ester, in which the addition molar number of the oxyalkylene group relative to 1 mole of sorbitol is 10 or more, preferably 15 or more, more preferably 20 or more, further preferably 25 or more, further more preferably 30 or more and further more preferably 35 or more, and 80 or less, preferably 65 or less, more preferably 60 or less, further preferably 55 or less and further more preferably 50 or less; the oxyalkylene group is preferably one or more kinds of groups selected from an oxyethylene group and an oxypropylene group, more preferably an oxyethylene group; the acyl group of the fatty acid has a carbon number of 8 or more, preferably 12 or more, more preferably 14 or more and further preferably 16 or more, and 22 or less, preferably 18 or less and more preferably 18; and the acyl group of the fatty acid is an acyl group of an unsaturated fatty acid.

<27> The sticking agent composition for agrochemicals described in any one of the above <1> to <26>, wherein the component C is contained in an amount of preferably 1% by mass or more, more preferably 2% by mass or more, further preferably 3% by mass or more and further more preferably 4% by mass; and preferably 12% by mass or less, more preferably 10% by mass or less, further preferably 9% by mass or less and further preferably 7% by mass or less.

<28> The sticking agent composition for agrochemicals described in any one of the above <1> to <27>, wherein a total content of the components A, B and C is preferably 10% by mass of more, more preferably 15% by mass or more, further preferably 20% by mass or more, further more preferably 30% by mass or more and further more preferably 38% by mass or more; and preferably 80% by mass or less, more preferably 70% by mass or less, further preferably 60% by mass or less, further more preferably 50% by mass or less and further more preferably 45% by mass or less.

<29> The sticking agent composition for agrochemicals described in any one of the above <1> to <28>, wherein water is contained in an amount of 16% by mass or more, more preferably 20% by mass or more, further preferably 30% or more, further more preferably 40% by more, further more preferably 50% by mass or more and further more preferably 55% by mass or more; and preferably 93.5% by mass or less, more preferably 90% by mass or less, further preferably 85% by mass or less, further more preferably 80% by mass or less, further more preferably 70% by mass or less and further more preferably 62% by mass or less.

<30> The sticking agent composition for agrochemicals described in any one of the above <1> to <29>, wherein the composition has a pH at 25° C. of preferably 2.0 or more, more preferably 3.0 or more, further preferably 3.5 or more and further more preferably 4.5 or more; and preferably 11 or less, more preferably 9 or less, further preferably 7 or less, further more preferably 6.5 or less and further more preferably 5.5 or less.

<31> The sticking agent composition for agrochemicals described in any one of the above <1> to <30>, wherein the composition has a viscosity at 25° C. of preferably 1.0 mPa·s or more, more preferably 2.0 mPa·s or more, further preferably 3.0 mPa·s or more, further more preferably 4.0 mPa·s or more and further more preferably 5.0 mPa·s or more; and preferably 10000 mPa·s or less, more preferably 1000 mPa·s or less, further preferably 100 mPa·s or less, further more preferably 50 mPa·s or less, further more preferably 30 mPa·s or less, further more preferably 20 mPa·s or less, further more preferably 15 mPa·s or less and further more preferably 13 mPa·s or less.

<32> The sticking agent composition for agrochemicals described in any one of the above <1> to <31>, wherein a mass ratio of the component A to the component B, component A/component B, is preferably 1 or more, more preferably 2 or more, further preferably 3 or more and further more preferably 4 or more; and preferably 30 or less, more preferably 20 or less, further preferably 10 or less and further more preferably 7 or less.

<33> The sticking agent composition for agrochemicals described in any one of the above <1> to <32>, wherein a mass ratio of the component A to the component C, component A/component C, is preferably 1 or more, more preferably 2 or more, further preferably 3 or more, further more preferably 4 or more and further more preferably 4.5 or more; and preferably 30 or less, more preferably 20 or less, further preferably 10 or less, further more preferably 8 or less, further more preferably 7 or less and further more preferably 6 or less.

<34> The sticking agent composition for agrochemicals described in any one of the above <1> to <33>, wherein a mass ratio of the component B to the component C, component B/component C, is preferably 0.1 or more, more preferably 0.2 or more, further preferably 0.5 or more, further more preferably 0.8 or more and further more preferably 1.0 or more; and preferably 5 or less, more preferably 3 or less, further preferably 2 or less and further more preferably 1.5 or less.

<35> The sticking agent composition for agrochemicals described in any one of the above <1> to <34>, wherein a mass ratio of the total of the components A and B to the component C, (component A+component B)/component C, is preferably 1 or more, more preferably 3 or more, further preferably 4 or more, further more preferably 6 or more and further more preferably 6.5 or more; and preferably 30 or less, more preferably 15 or less, further preferably 10 or less, further preferably 8 or less and further preferably 7.5 or less.

<36> The sticking agent composition for agrochemicals described in any one of the above <1> to <35>, wherein a mass ratio of the component A to the total of the components B and C, component A/(component B+component C), is preferably 0.5 or more, more preferably 1.0 or more, further preferably 1.5 or more, further more preferably 2.0 or more and further more preferably 2.4 or more; and preferably 6.0 or less, more preferably 5.0 or less, further preferably 4.5 or less, further more preferably 3.5 or less and further more preferably 3.0 or less.

<37> The sticking agent composition for agrochemicals described in any one of the above <1> to <36>, wherein the composition is prepared by mixing the components A, B and C, and gradually adding a predetermined amount of water while stirring, and preferably the composition is prepared at a temperature of preferably 30° C. or more and 100° C. or less, more preferably 40° C. or more and 90° C. or less, and further preferably 50° C. or more and 80° C. or less by mixing the components A, B and C, and gradually adding a predetermined amount of water while stirring.

<38> An agrochemical composition, wherein an agrochemical technical product and the sticking agent composition for agrochemicals described in any one of the above <1> to <37> are formulated.

<39> The agrochemical composition described in the above <38>, wherein the agrochemical technical product is any of agrochemical technical products selected from individual active ingredients of fungicides, insecticides, miticides and herbicides.

<40> The agrochemical composition described in the above <39>, wherein the fungicide is selected from basic copper sulfate, an organocopper compound (Oxine-copper) and cupric hydroxide, preferably basic copper sulfate.

<41> The agrochemical composition described in the above <39>, wherein the insecticide is selected from permethrin, DDVP (dimethyl 2,2-dichlorovinylphosphate), methomyl (S-methyl N-[(methylcarbamoyl)oxy]thioacetimide), and acephate (O,S-dimethyl N-acetyl phosphoramidothioate), preferably acephate.

<42> The agrochemical composition described in the above <39>, wherein the herbicide is selected from DBN (2,6-dichlorobenzonitrile), DCMU (3-(3,4-dichlorophenyl)-1,1-dimethylurea), paraquat (1,1'-dimethyl-4,4'-bipyridinium dichloride), diquat (6,7-dihydrodipyrido[1,2-a:2',1'c]pyrazinediium dibromide) and glyphosate (N-(phosphonomethyl)glycine and salts thereof), preferably glyphosate.

<43> The agrochemical composition described in the above <39>, wherein the miticide is selected from phenisobromolate (4,4'-dibromobenzilic acid isopropyl ester), amitraz(3-methyl-1,5-bis(2,4-xylyl)-1,3,5-triazapenta-1,4-diene) and fenpyroximate (tert-butyl=(E)-α-(1,3-dimethyl-5-phenoxypyrazol-4-ylmethyleneaminooxy-p-toluate).

<44> The agrochemical composition described in any one of the above <38> to <43>, wherein a formulation concentration of the agrochemical technical product in the agrochemical composition is preferably 10 ppm or more, more preferably 100 ppm or more and further preferably 500 ppm or more; and preferably 200000 ppm or less, more preferably 50000 ppm or less and further preferably 30000 ppm or less.

<45> The agrochemical composition described in any one of the above <38> to <44>, wherein a formulation concentration of the sticking agent composition for agrochemicals in the agrochemical composition is preferably 100 ppm or more, more preferably 500 ppm or more and further preferably 1000 ppm or more; and preferably 20000 ppm or less, more preferably 10000 ppm or less and further preferably 4000 ppm or less.

<46> The agrochemical composition described in any one of the above <38> to <45>, wherein a formulation concentration of the component A in the agrochemical composition is preferably 50 ppm or more, more preferably 150 ppm or more, further preferably 200 ppm or more and further more preferably 300 ppm or more; and preferably 15000 ppm or less, more preferably 5000 ppm or less, further preferably 1000 ppm or less and further more preferably 800 ppm or less.

<47> The agrochemical composition described in any one of the above <38> to <46>, wherein a formulation concentration of the component B in the agrochemical composition is preferably 15 ppm or more, more preferably 20 ppm or more, further preferably 50 ppm or more and further more preferably 80 ppm or more; and preferably 2000 ppm or less, more preferably 1000 ppm or less, further preferably 500 ppm or less, further more preferably 300 ppm or less and further more preferably 180 ppm or less 0.

<48> The agrochemical composition described in any one of the above <38> to <47>, wherein a formulation concentration of the component C in the agrochemical composition is preferably 15 ppm or more, more preferably 50 ppm or more, further preferably 80 ppm or more and further preferably 80 ppm or more; and preferably 2000 ppm or less, more preferably 1000 ppm or less, further preferably 500 ppm or less, further more preferably 300 ppm or less and further preferably 180 ppm or less.

<49> A method for enhancing effects of an agrochemical, including applying, to an object, an agrochemical technical product selected from agrochemical technical products such as fungicides, insecticides, miticides and herbicides together with the sticking agent composition for agrochemicals described in any one of the above <1> to <37>.

<50> A method for improving rain proof of an agrochemical, including applying, to an object, an agrochemical technical product selected from agrochemical technical products such as fungicides, insecticides, miticides and herbicides together with the sticking agent composition for agrochemicals described in any one of the above <1> to <37>.

<51> A method for improving sticking property of an agrochemical, including applying, to an object, an agrochemical technical product selected from agrochemical technical products such as fungicides, insecticides, miticides and herbicides together with the sticking agent composition for agrochemicals described in any one of the above <1> to <37>.

<52> A method for producing a sticking agent composition for agrochemicals, including mixing the following components A, B and C, and water, Component A: a fatty acid triglyceride represented by the following formula (A), $$\begin{array}{l} CH_2OR^1 \\ | \\ CHOR^2 \\ | \\ CH_2OR^3 \end{array} \qquad \text{Formula (A)}$$

in the formula, $R^1$, $R^2$ and $R^3$ are the same or different and denote an acyl group with 8 or more and 18 or less carbon atoms, Component B: a fatty acid represented by the following formula (B), $$R^{1b}\text{—COOH} \qquad \text{Formula (B)}$$

in the formula, $R^{1b}$ denotes an alkyl group with 11 or more and 19 or less carbon atoms or an alkenyl group with 11 or more and 19 or less carbon atoms, and Component C: a polyoxyalkylene sorbitol fatty acid ester <53> A method for producing a sticking agent composition for agrochemicals described in the above <52>, including mixing the components A, B and C at preferably 30° C. or higher, more preferably 40° C. or higher and further preferably 50° C. or higher; and preferably 100° C. or lower, more preferably 90° C. or lower and further preferably 80° C. or lower; and mixing the obtained mixture with water having a temperature of preferably 30° C. or higher, more preferably 40° C. or higher and further preferably 50° C. or higher; and preferably 100° C. or lower, more preferably 90° C. or lower and further preferably 80° C. or lower.

<54> The method for producing a sticking agent composition for agrochemicals described in the above <52> or <53>, whereby the sticking agent composition for agrochemicals described in any one of the above <1> to <37> is obtained.

The matters described on the sticking agent composition for agrochemicals described in any one of the above <1> to <37> can be applied to the methods for producing a sticking agent composition for agrochemicals of the above <52> to <54>.

<55> A method for producing an agrochemical composition, including mixing an agrochemical technical product, the following components A, B and C, and water, Component A: a fatty acid triglyceride represented by the following formula (A), $$\begin{array}{l} CH_2OR^1 \\ | \\ CHOR^2 \\ | \\ CH_2OR^3 \end{array} \qquad \text{Formula (A)}$$

in the formula, $R^2$, $R^2$ and $R^3$ are the same or different and denote an acyl group with 8 or more and 18 or less carbon atoms, Component B: a fatty acid represented by the following formula (B), $$R^{1b}\text{—COOH} \qquad \text{Formula (B)}$$

in the formula, $R^{1b}$ denotes an alkyl group with 11 or more and 19 or less carbon atoms or an alkenyl group with 11 or more and 19 or less carbon atoms, and Component C: a polyoxyalkylene sorbitol fatty acid ester <56> The method for producing an agrochemical composition described in the above <55>, whereby the agrochemical composition described in any one of the above <38> to <49> is obtained.

The matters described on the agrochemical composition of the above <38> to <49> can be applied to the methods for producing the agrochemical composition of <55> to <56>.

Examples

Hereinafter, the present invention will be further explained by referring to Examples and Comparative Examples. The Examples are for illustrating the present invention, and not for limiting the present invention.

Synthesis Examples for C(2), C(4) to C(9)

Ethylene oxide (hereinafter expressed as EO) was added to sorbitol by a conventional method, and polyoxyethylene (EO addition molar number of sorbitol per hydroxyl group=5) sorbitol was obtained. 1132.6 g of this polyoxyethylene sorbitol, 906.6 g of oleic acid and 7.0 g of 48% by mass of aqueous sodium hydroxide were fed into a four-neck flask for nitrogen substitution, and then esterification was conducted at 225° C. under nitrogen stream. It was confirmed that the acid value was 8 or less, and cooling to 60° C. was performed. After about 3 hours from the start of reaction, the acid value became 8 or less. After the cooling, 14.9 g of water was added, and then 8.40 g of 90% by mass of lactic acid aqueous solution (one equivalent relative to sodium hydroxide used for esterification reaction) was added, stirring was conducted for one hour, and a composition containing polyoxyethylene sorbitol fatty acid ester [C(2)] was obtained. Polyoxyethyelen sorbitol fatty acid ester contained in the composition is a tetraester compound, and the average addition molar number of EO to sorbitol was 20 (EO addition molar number of sorbitol per hydroxyl group=5). This compound is indicated as "POE (20) sorbitol tetra oleic acid ester" in the table.

Various polyoxyalkylene sorbitol fatty acid esters [C(4) to C(9)] shown in the same table as the above were synthesized by using polyoxyethylene sorbitols having different EO addition molar numbers or fatty acids other than oleic acid, or by changing a feeding amount or the like. In the table, numbers in parentheses next to POE indicate average addition molar numbers of EO to sorbitol.

Examples 1 to 27 and Comparative Examples 1 to 12

[Preparation of Sticking Agent Composition for Agrochemicals]

Components used for Examples and Comparative Examples are indicated in Table 1.

Components A, B and C were mixed at 60° C. so that they are contained in predetermined amounts shown in Table 2 or Table 3, a predetermined amount of 60° C. water was gradually added while stirring, and cooling to the room temperature resulted in the preparation of sticking agent compositions for agrochemicals in Table 2 or Table 3.

[Test 1 Sticking Test of Fungicide]

A seedling of citrus (variety: Nichinan Ichi-go) was transplanted in a 30-cm pot and grown for half a year, and then a citrus with a height of 1 m was prepared.

IC Bordeaux 66D as an fungicide (fungicidal component: copper, commercial product, Inoue Calcium Corporation) was formulated with a sticking agent composition in Table 2 or Table 3, and water, so that an agrochemical composition having an agrochemical concentration of 20000 ppm and a sticking agent composition concentration of 2000 ppm was obtained. In this agrochemical composition, the fungicide was diluted by 50 times and the sticking agent composition was diluted by 500 times. This agrochemical composition was sprayed onto leaves in a spraying amount of 100 L per 10 are.

From the day following the date of the spraying, artificial rainfall (30 mm for 5 minutes for one time) by an applicator was provided daily for 6 days. After 8 days have passed, 10 leaves of citrus were collected from each area. Agrochemical components were extracted from surfaces of the leaves with 0.1 N hydrochloric acid, and then Cu as a fungicide component was analyzed by ICP. Leaves used for extraction were photographed, their areas were measured by image processing, and a Cu amount per area that remained on leaf surfaces was calculated. As a control, an amount of Cu in an IC Bordeaux-treated area with no artificial rainfall treatment (non-rainfall-treated area) was calculated. The sticking ratio of Cu as a fungicide was calculated by the following equation.

Sticking ratio (%)=(Cu amount of each of rainfall-treated areas/Cu amount of non-rainfall-treated area)×100

From results of Tables 2 and 3, it has been found that products of the present invention have high performance for allowing insecticides to stick.

[Test 2 Sticking Test of Insecticide]

A cabbage was grown in 12 cm pot until it reached to 6-leaf stage.

Altran wettable powder (insecticidal component: acephate, commercial product, Hokko Chemical Industry Co., Ltd.) was formulated with a sticking agent composition of Table 2 or Table 3 and water, so that an agrochemical composition having an agrochemical concentration of 1000 ppm and a sticking agent composition concentration of 2000 ppm was obtained. In this agrochemical compositions, the insecticide was diluted by 1000 times and the sticking agent composition was diluted by 500 times. This agrochemical composition was sprayed onto leaves in a spraying amount of 100 L per 10 are.

From the day following the date of the spraying, artificial rainfall (30 mm for 5 minutes) by an applicator was provided one time. After being dried, 3 leaves of cabbage were collected from each area, and agrochemical components were extracted from surfaces of leaves with water. Extracts were subjected to solid-phase extraction by use of an activated carbon cartridge, and then analysis on acephate as the insecticidal component was conducted by GC/MS method. At that time, target substances were collected by flow of water through the activated carbon cartridge column (rate: 10 ml/min), and then the target substances were eluted with 5 mL of dichloromethane and concentrated under nitrogen stream. Thereafter, an amount of acephate was measured by GC/MS.

Conditions for GC/MS were as follows.
Conditions for gas chromatograph (GC)
  Column: 50% phenyl methyl silicon type
  Inner diameter: 0.2 to 0.3 mm
  Length: 20 to 30 m
  Carrier gas: high-purity helium
  Flow rate: 1 mL/min
  Column temperature:
    70° C. (1 min)→30° C./min increase→200° C.→+10° C./min increase→250° C.
  Temperature at injection port: 250° C.
Conditions for Mass Spectrometry (MS)
  Ionization method: electron impact ionization method
  Ion voltage: 70 eV
  Ion source temperature: 230° C.
  Interface temperature: 250° C.
  Measured ion: acephate, mass number: 183.17
  Monitor ion: m/z, quantity: 136

Leaves used for extraction were photographed, their areas were measured by image processing, and an amount of acephate per area that remained on leaf surfaces was calculated. As a control, an amount of acephate in an Altran wettable powder-treated area with no artificial rainfall treatment (non-rainfall-treated area) was calculated. The sticking ratio of acephate as an insecticide was calculated by the following equation.

Sticking ratio (%)=(acephate amount of each of rainfall-treated areas/acephate amount of non-rainfall-treated area)×100

From results of Tables 2 and 3, it has been found that products of the present invention have high performance for allowing insecticides to stick.

[Test 3 Sticking Test of Herbicide]

A barnyard grass was grown in a 12 cm pot until it reached to 6-leaf stage.

ROUNDUP MAXLOAD® as a herbicide (herbicidal component: glyphosate, commercial product, Nissan Chemical Industries, Ltd.) was formulated with a sticking agent composition of Table 2 or Table 3 and water, so that an agrochemical composition having an agrochemical concentration of 10000 ppm and a sticking agent composition concentration of 2000 ppm was obtained. In this agrochemical composition, the herbicide was diluted by 100 times and the sticking agent composition was diluted by 500 times. This agrochemical composition was sprayed onto leaves in a spraying amount of 100 L per 10 are.

From the day following the date of the spraying, artificial rainfall (30 mm for 5 minutes) by an applicator was provided one time. After being dried, 3 leaves of barnyard grass were collected from each area, and agrochemical components were extracted from surfaces of leaves with water. Thereafter, analysis on glyphosate as the herbicidal component was conducted by ion chromatography method.

Measurement conditions for ion chromatography were as follows.

Apparatus: Dionex ICS-2000
Separation column: Dionex Ion Pac AS18 4×250 mm
Eluant: KOH solution
Eluant gradient condition: 20 mmol/L (5 min)→40 mmol/L (8 min)→50 mmol/L (30 min)
Eluant flow rate: 1.0 ml/min
Column temperature: 45° C.
Sample injection amount: 200 μL
Detector: electric conductivity Leaves used for extraction were photographed, their areas were measured by image processing, and an amount of glyphosate per area that remained on leaf surfaces was calculated. As a control, an amount of Cu in a ROUNDUP MAXLOAD®-treated area with no artificial rainfall treatment (non-rainfall-treated area) was calculated. The sticking ratio of glyphosate as an herbicide was calculated by the following equation.

Sticking ratio (%)=(glyphosate amount of each of rainfall-treated areas/glyphosate amount of non-rainfall-treated area)×100

From results of Tables 2 and 3, it has been found that products of the present invention have high performance for allowing herbicides to stick.

[Test 4 Formulation Stability Test]

Sticking agent compositions of Table 2 or Table 3 were allowed to stand in a thermostat bath at 50° C., and formulation stability test was conducted. Measurement was conducted for 90 days and whether a sticking agent composition is separated or not is determined by visual observation, and the number of days until the separation was measured and recorded. When separation occurred immediately after the preparation of a composition, it is recorded as zero day. When no separation occurred during the measurement period, it is recorded as 90 days. As a result, the product of the present invention exhibited emulsification stability for a longer period than comparative products.

TABLE 1

| Symbol | Compound | Details |
|---|---|---|
| Component A | | |
| A(1) | Caprylic acid triglyceride | Kao Corporation, Product name: COCONARD RK |
| A(2) | Caprylic acid capric acid triglyceride | Kao Corporation, Product name: COCONARD MT |
| A(3) | Coconut oil | Yamakei Sangyo K.K., Product name: coconut oil |
| A(4) | Palm oil | Yamakei Sangyo K.K., Product name: palm oil |
| A(5) | Palm kernel oil | Yamakei Sangyo K.K., Product name: palm kernel oil |
| A(6) | Rice bran oil | Kaneda Co., Ltd., Product name: rice bran oil |
| A(7) | Corn oil | Kaneda Co., Ltd., Product name: corn oil |
| A(8) | Rapeseed oil | Kaneda Co., Ltd., Product name: rapeseed oil |
| A(9) | Soybean oil | Wako Pure Chemical Industries, Ltd., Product name: soybean oil |
| A'(1) | Tricaproin | Tokyo Chemical Industry Co., Ltd., Product name: tricaproin |
| A'(2) | Triarachidin | Tokyo Chemical Industry Co., Ltd., Product name: triarachidin |
| Component B | | |
| B(1) | Oleic acid | Kao Corporation, Product name: LUNAC O-V |
| B(2) | Lauric acid | Kao Corporation, Product name: LUNAC L-98 |
| B(3) | Palmitic acid | Kao Corporation, Product name: LUNAC P-95 |
| B(4) | Myristic acid | Kao Corporation, Product name: LUNAC MY-98 |
| B'(1) | Behenic acid | Wako Pure Chemical Industries, Ltd. |
| Component C | | |
| C(1) | POE(40) sorbitol tetra oleic acid ester | Kao Corporation, Product name: RHEODOL 440V |
| C(2) | POE(20) sorbitol tetra oleic acid ester | Synthetic material |
| C(3) | POE(60) sorbitol tetra oleic acid ester | Kao Corporation, Product name: RHEODOL 460V |
| C(4) | POE(40) sorbitol penta oleic acid ester | Synthetic material |
| C(5) | POE(40) sorbitol tetra lauric acid ester | Synthetic material |
| C(6) | POE(40) sorbitol tetra stearic acid ester | Synthetic material |
| C(7) | POE(40) sorbitol mono oleic acid ester | Synthetic material |
| C(8) | POE(40) sorbitol di oleic acid ester | Synthetic material |
| C(9) | POE(40) sorbitol tri oleic acid ester | Synthetic material |

TABLE 1-continued

| Symbol | Compound | Details |
|---|---|---|
| C(10) | POE(30) sorbitol tetra oleic acid ester | Kao Corporation, Product name: RHEODOL 430V |
| C'(1) | POE(20)sorbitan mono oleic acid ester | Kao Corporation, Product name: RHEODOL TW-O120V |

Caprylic acid capric acid triglyceride shown in the column for component A is a triglyceride of glycerin and mixed fatty acid of caprylic acid and capric acid, and the mass ratio of caprylic acid to capric acid as fatty acid composition was 82/18.

Further, regarding coconut oil, palm oil, palm kernel oil, rice bran oil, corn oil, rapeseed oil and soybean oil shown in the column for component A, carbon numbers of their main constituent fatty acids and their ratio are indicated below. These numerical values are analytical values at the time of the tests. C is an abbreviation of carbon number, and numerals next to it signify a number of carbon atoms. Further, numeral values in parentheses are ratios (% by mass) of the above oils in the entire constituent fatty acids. These oils all had a composition of constituent fatty acids of 8 or more and 18 or less, and $R^1$, $R^2$ and $R^3$ in the formula (A) were an acyl group with 8 or more and 18 or less carbon atoms. Therefore, the content ratio of component A was 100% by mass.

Coconut oil: C8 (8%), C10 (8%), C12 (47%), C14 (19%), C16 (7%) and C18 (11%)
Palm oil: C14 (2%), C16 (41%) and C18 (57%)
Palm kernel oil: C8 (4%), C10 (5%), C12 (52%), C14 (14%), C16 (9%) and C18 (16%)
Rice bran oil: C14 (1%), C16 (16%) and C18 (83%)
Corn oil: C16 (10%) and C18 (90%)
Rapeseed oil: C16 (4%) and C18 (96%)
Soybean oil: C16 (8%) and C18 (92%)

Further, A'(1) or tricaproin, and A'(2) or triarachidin are not categorized as the component A. However, as a matter of convenience, they are indicated in the column for component A and regarded as the component A, and mass ratios of component A/(component B+component C) are indicated in Table 3.

Further, B' (1) or behenic acid is not categorized as the component B. However, as a matter of convenience, it is indicated in the column for component B and regarded as the component B, and a mass ratio of component A/(component B+component C) is indicated in Table 3.

Also, C'(1) or PEO (20) sorbitan mono oleic acid ester is not categorized as the component C. However, as a matter of convenience, it is indicated in the column for component C and regarded as the component C, and a mass ratio of component A/(component B+component C) is indicated in Table 2.

TABLE 2

| | | Sticking agent composition for agrochemicals | | | | | | | | |
|---|---|---|---|---|---|---|---|---|---|---|
| | | Component A | | Component B | | Component C | | Water | | | |
| | | Symbol | Content (% by mass) | Symbol | Content (% by mass) | Symbol | Content (% by mass) | Content (% by mass) | A/(B + C) (mass ratio) | pH | Viscosity (mPa · s) |
| Examples | 1 | A(1) | 30 | B(1) | 6 | C(1) | 5 | 59 | 2.7 | 5.0 | 6.5 |
| | 2 | A(2) | 30 | B(1) | 6 | C(1) | 5 | 59 | 2.7 | 5.0 | 7.4 |
| | 3 | A(3) | 30 | B(1) | 6 | C(1) | 5 | 59 | 2.7 | 5.0 | 10.5 |
| | 4 | A(4) | 30 | B(1) | 6 | C(1) | 5 | 59 | 2.7 | 5.0 | 12.0 |
| | 5 | A(5) | 30 | B(1) | 6 | C(1) | 5 | 59 | 2.7 | 5.0 | 10.2 |
| | 6 | A(6) | 30 | B(1) | 6 | C(1) | 5 | 59 | 2.7 | 5.0 | 13.1 |
| | 7 | A(7) | 30 | B(1) | 6 | C(1) | 5 | 59 | 2.7 | 5.0 | 13.2 |
| | 8 | A(8) | 30 | B(1) | 6 | C(1) | 5 | 59 | 2.7 | 5.0 | 13.2 |
| | 9 | A(9) | 30 | B(1) | 6 | C(1) | 5 | 59 | 2.7 | 5.0 | 13.1 |
| | 10 | A(2) | 10 | B(1) | 6 | C(1) | 5 | 79 | 0.9 | 5.0 | 4.5 |
| | 11 | A(2) | 50 | B(1) | 6 | C(1) | 5 | 39 | 4.5 | 5.0 | 25.0 |
| | 12 | A(2) | 30 | B(1) | 1 | C(1) | 5 | 64 | 5.0 | 5.8 | 18.0 |
| | 13 | A(2) | 30 | B(1) | 9 | C(1) | 5 | 56 | 2.1 | 4.2 | 9.0 |
| | 14 | A(2) | 30 | B(1) | 6 | C(2) | 5 | 59 | 2.7 | 5.0 | 10.2 |
| | 15 | A(2) | 30 | B(1) | 6 | C(3) | 5 | 59 | 2.7 | 5.0 | 8.1 |
| | 16 | A(2) | 30 | B(1) | 6 | C(4) | 5 | 59 | 2.7 | 5.0 | 10.5 |
| | 17 | A(2) | 30 | B(1) | 6 | C(5) | 5 | 59 | 2.7 | 5.0 | 13.1 |
| | 18 | A(2) | 30 | B(1) | 6 | C(6) | 5 | 59 | 2.7 | 5.0 | 75.5 |
| | 19 | A(2) | 30 | B(1) | 6 | C(7) | 5 | 59 | 2.7 | 5.0 | 12.1 |
| | 20 | A(2) | 30 | B(1) | 6 | C(1) | 3 | 61 | 3.3 | 5.0 | 15.5 |
| | 21 | A(2) | 30 | B(1) | 6 | C(1) | 9 | 55 | 2.0 | 5.0 | 6.1 |
| | 22 | A(2) | 30 | B(2) | 6 | C(1) | 5 | 59 | 2.7 | 4.7 | 7.4 |
| | 23 | A(2) | 30 | B(3) | 6 | C(1) | 5 | 59 | 2.7 | 6.1 | 40.0 |
| Comparative Examples | 1 | Agrochemical alone (no rainfall treatment) | | | | | | | | | |
| | 2 | Agrochemical alone (with rainfall treatment) | | | | | | | | | |
| | 3 | A(2) | 30 | — | — | — | — | 70 | — | 7.0 | 51.5 |
| | 4 | — | — | B(1) | 6 | — | — | 94 | 0 | 4.9 | 3.4 |
| | 5 | — | — | — | — | C(1) | 5 | 95 | 0 | 6.5 | 2.5 |
| | 6 | A(2) | 30 | B(1) | 6 | — | — | 64 | 5.0 | 5.0 | 48.0 |
| | 7 | A(2) | 30 | — | — | C(1) | 5 | 65 | 6.0 | 6.6 | 8.4 |

TABLE 2-continued

| | | | | | | | | | | |
|---|---|---|---|---|---|---|---|---|---|---|
| 8 | — | — | B(1) | 6 | C(1) | 5 | 89 | 0 | 5.0 | 3.0 |
| 9 | A(2) | 30 | B(1) | 6 | C'(1) | 5 | 59 | 2.7 | 5.0 | 34.4 |

| | | Conc. (ppm) in agrochemical composition (500 times dilution) | | | Sticking ratio (%) | | | Formulation Stability |
|---|---|---|---|---|---|---|---|---|
| | | | | | Test 1 | Test 2 | Test 3 | Test 4 |
| | | Component A | Component B | Component C | Fungicide | Insecticide | Herbicide | (days) |
| Examples | 1 | 600 | 120 | 100 | 88 | 86 | 90 | 90 |
| | 2 | 600 | 120 | 100 | 92 | 89 | 94 | 90 |
| | 3 | 600 | 120 | 100 | 90 | 87 | 91 | 84 |
| | 4 | 600 | 120 | 100 | 86 | 82 | 89 | 75 |
| | 5 | 600 | 120 | 100 | 89 | 87 | 90 | 83 |
| | 6 | 600 | 120 | 100 | 86 | 83 | 88 | 83 |
| | 7 | 600 | 120 | 100 | 83 | 80 | 85 | 77 |
| | 8 | 600 | 120 | 100 | 86 | 83 | 88 | 80 |
| | 9 | 600 | 120 | 100 | 82 | 78 | 84 | 76 |
| | 10 | 200 | 120 | 100 | 65 | 62 | 67 | 47 |
| | 11 | 1000 | 120 | 100 | 78 | 75 | 80 | 50 |
| | 12 | 600 | 20 | 100 | 75 | 73 | 77 | 49 |
| | 13 | 600 | 180 | 100 | 82 | 78 | 83 | 63 |
| | 14 | 600 | 120 | 100 | 80 | 76 | 82 | 74 |
| | 15 | 600 | 120 | 100 | 83 | 79 | 86 | 85 |
| | 16 | 600 | 120 | 100 | 83 | 78 | 85 | 67 |
| | 17 | 600 | 120 | 100 | 75 | 72 | 78 | 61 |
| | 18 | 600 | 120 | 100 | 70 | 66 | 73 | 51 |
| | 19 | 600 | 120 | 100 | 73 | 70 | 74 | 71 |
| | 20 | 600 | 120 | 60 | 81 | 77 | 83 | 48 |
| | 21 | 600 | 120 | 180 | 85 | 81 | 88 | 60 |
| | 22 | 600 | 120 | 100 | 67 | 63 | 73 | 66 |
| | 23 | 600 | 120 | 100 | 81 | 78 | 84 | 48 |
| Comparative Examples | 1 | Agrochemical alone (no rainfall treatment) | | | 100 | 100 | 100 | — |
| | 2 | Agrochemical alone (with rainfall treatment) | | | 20 | 15 | 22 | — |
| | 3 | 600 | — | — | 25 | 21 | 28 | 0 |
| | 4 | — | 120 | — | 30 | 24 | 32 | 0 |
| | 5 | — | — | 100 | 15 | 10 | 18 | 1 |
| | 6 | 600 | 120 | — | 34 | 30 | 37 | 0 |
| | 7 | 600 | — | 100 | 41 | 35 | 43 | 15 |
| | 8 | — | 120 | 100 | 36 | 31 | 38 | 10 |
| | 9 | 600 | 120 | 100 | 44 | 37 | 45 | 20 |

TABLE 3

| | | Sticking agent composition for agrochemicals | | | | | | | | |
|---|---|---|---|---|---|---|---|---|---|---|
| | | Component A | | Component B | | Component C | | Water | | |
| | | Symbol | Content (% by mass) | Symbol | Content (% by mass) | Symbol | Content (% by mass) | Content (% by mass) | A/(B + C) (mass ratio) | pH | Viscosity (mPa·s) |
| Examples | 24 | A(2) | 30 | B(4) | 6 | C(1) | 5 | 59 | 2.7 | 4.9 | 5.3 |
| | 25 | A(2) | 30 | B(1) | 6 | C(8) | 5 | 59 | 2.7 | 5.0 | 10.5 |
| | 26 | A(2) | 30 | B(1) | 6 | C(9) | 5 | 59 | 2.7 | 5.0 | 8.3 |
| | 27 | A(2) | 30 | B(1) | 6 | C(10) | 5 | 59 | 2.7 | 5.0 | 8.0 |
| Comparative Examples | 10 | A'(1) | 30 | B(1) | 6 | C(1) | 5 | 59 | 2.7 | 5.0 | 3.2 |
| | 11 | A'(2) | 30 | B(1) | 6 | C(1) | 5 | 59 | 2.7 | 5.0 | 26.3 |
| | 12 | A(2) | 30 | B'(1) | 6 | C(1) | 5 | 59 | 2.7 | 5.0 | 21.5 |

| | | Conc. (ppm) in agrochemical composition (500 times dilution) | | | Sticking ratio (%) | | | Formulation stability |
|---|---|---|---|---|---|---|---|---|
| | | | | | Test 1 | Test 2 | Test 3 | Test 4 |
| | | Component A | Component B | Component C | Fungicide | Insecticide | Herbicide | (days) |
| Examples | 24 | 600 | 120 | 100 | 78 | 76 | 81 | 60 |
| | 25 | 600 | 120 | 100 | 74 | 71 | 75 | 72 |
| | 26 | 600 | 120 | 100 | 88 | 86 | 91 | 86 |
| | 27 | 600 | 120 | 100 | 86 | 84 | 88 | 88 |
| Comparative Examples | 10 | 600 | 120 | 100 | 43 | 38 | 45 | 20 |
| | 11 | 600 | 120 | 100 | 45 | 40 | 47 | 23 |
| | 12 | 600 | 120 | 100 | 43 | 39 | 43 | 22 |

In the tables, A/(B+C) (mass ratio) is component A/(component B+component C) (mass ratio). Further, in the tables, the content of each component is an effective content. Furthermore, in the tables, pH values and viscosity values were all measured at 25° C.

The invention claimed is:

1. A method for enhancing effects of an agrochemical, comprising applying, to an object, an agrochemical technical product together with a sticking agent composition for agrochemicals comprising the following components A, B and C, and water, component A: a fatty acid triglyceride represented by the following formula (A),

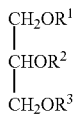

Formula (A)

wherein $R^1$, $R^2$ and $R^3$ are the same or different and denote an acyl group with 8 or more and 18 or less carbon atoms, component B: a fatty acid represented by the following formula (B),

Formula (B)

wherein $R^{1b}$ denotes an alkyl group with 11 or more and 19 or less carbon atoms or an alkenyl group with 11 or more and 19 or less carbon atoms, and component C: a polyoxyethylene sorbitol fatty acid ester, wherein the component C polyoxyethylene sorbitol fatty acid ester has an addition molar number of oxyethylene group relative to 1 mole of sorbitol of 20 or more and 60 or less, and the fatty acid has an acyl group having a carbon number of 12 or more and 18 or less.

2. A method for improving rain proof of an agrochemical, comprising applying, to an object, an agrochemical technical product together with a sticking agent composition for agrochemicals comprising the following components A, B and C, and water, component A: a fatty acid triglyceride represented by the following formula (A),

Formula (A)

wherein $R^1$, $R^2$ and $R^3$ are the same or different and denote an acyl group with 8 or more and 18 or less carbon atoms, component B: a fatty acid represented by the following formula (B),

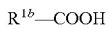

Formula (B)

wherein $R^{1b}$ denotes an alkyl group with 11 or more and 19 or less carbon atoms or an alkenyl group with 11 or more and 19 or less carbon atoms, and component C: a polyoxyethylene sorbitol fatty acid ester, wherein the component C polyoxyethylene sorbitol fatty acid ester has an addition molar number of oxyethylene group relative to 1 mole of sorbitol of 20 or more and 60 or less, and the fatty acid has an acyl group having a carbon number of 12 or more and 18 or less.

3. A method for improving sticking property of an agrochemical, comprising applying, to an object, an agrochemical technical product together with a sticking agent composition for agrochemicals comprising the following components A, B and C, and water, component A: a fatty acid triglyceride represented by the following formula (A),

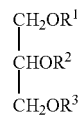

Formula (A)

wherein $R^1$, $R^2$ and $R^3$ are the same or different and denote an acyl group with 8 or more and 18 or less carbon atoms, component B: a fatty acid represented by the following formula (B),

Formula (B)

wherein $R^{1b}$ denotes an alkyl group with 11 or more and 19 or less carbon atoms or an alkenyl group with 11 or more and 19 or less carbon atoms, and component C: a polyoxyethylene sorbitol fatty acid ester, wherein the component C polyoxyethylene sorbitol fatty acid ester has an addition molar number of oxyethylene group relative to 1 mole of sorbitol of 20 or more and 60 or less, and the fatty acid has an acyl group having a carbon number of 12 or more and 18 or less.

4. A method according to claim 1, comprising using the sticking agent composition for agrochemicals at the time of diluted use of an agrochemical containing an agrochemical technical product and not containing the sticking agent composition for agrochemicals.

5. The method according to claim 1, wherein a mass ratio of the component A to a total of the components B and C, component A/(component B+component C), is 0.5 or more and 5.0 or less.

6. The method according to claim 1, wherein the component A is a fatty acid triglyceride, in which $R^1$, $R^2$ and $R^3$ in the formula (A) are each an acyl group with 8 or more and 12 or less carbon atoms.

7. The method according to claim 1, wherein the component B is a fatty acid, in which $R^{1b}$ in the formula (B) is an alkyl group with 13 or more and 17 or less carbon atoms or an alkenyl group with 13 or more and 17 or less carbon atoms.

8. The method according to claim 1, wherein the component B is oleic acid.

9. The method according to claim 1, wherein the component C is one or more of polyoxyethylene sorbitol fatty acid esters selected from the group consisting of:

(C1) a polyoxyethylene sorbitol tri-fatty acid ester, wherein the addition molar number of the oxyethylene group relative to 1 mole of sorbitol is 20 or more and 60 or less, and the fatty acid forming the component C is an unsaturated fatty acid with 14 or more and 18 or less carbon atoms;

(C2) a polyoxyethylene sorbitol tetra-fatty acid ester, wherein the addition molar number of the oxyethylene group relative to 1 mole of sorbitol is 20 or more and 60 or less, and the fatty acid forming the component C is an unsaturated fatty acid with 14 or more and 18 or less carbon atoms; and (C3) a polyoxyethylene sorbitol penta-fatty acid ester, wherein the addition molar number of the oxyethylene group relative to 1 mole of sorbitol is 20 or more and 60 or less, and the fatty acid forming the component C is an unsaturated fatty acid with 14 or more and 18 or less carbon atoms.

10. The method according to claim 1, wherein the component C is one or more of polyoxyethylene sorbitol fatty acid esters selected from the group consisting of:

(C1-1) a polyoxyethylene sorbitol tri-fatty acid ester, wherein the addition molar number of the oxyethylene group relative to 1 mole of sorbitol is 30 or more and 60 or less, and the fatty acid forming the component C is oleic acid;

(C2-1) a polyoxyethylene sorbitol tetra-fatty acid ester, wherein the addition molar number of the oxyethylene group relative to 1 mole of sorbitol is 30 or more and 60 or less, and the fatty acid forming the component C is oleic acid; and (C3-1) a polyoxyethylene sorbitol penta-fatty acid ester, wherein the addition molar number of the oxyethylene group relative to 1 mole of sorbitol is 30 or more and 60 or less, and the fatty acid forming the component C is oleic acid.

11. The method according to claim 1, comprising using an agrochemical composition containing the agrochemical technical product and the sticking agent composition for agrochemicals.

12. The method according to claim 1, wherein the agrochemical technical product and the sticking agent composition for agrochemicals are mixed, emulsified and dispersed.

13. The method according to claim 1, wherein the agrochemical technical product is selected from the group consisting of fungicides, insecticides, miticides and herbicides.

14. The method according to claim 11, wherein the concentration of the agrochemical technical product in the agrochemical composition is 10 ppm or more and 200000 ppm or less.

15. The method according to claim 11, wherein the concentration of the component A in the agrochemical composition is 50 ppm or more and 15000 ppm or less.

16. The method according to claim 11, wherein the concentration of the component B in the agrochemical composition is 15 ppm or more and 2000 ppm or less.

17. The method according to claim 11, wherein the concentration of the component C in the agrochemical composition is 15 ppm or more and 2000 ppm or less.

18. The method according to claim 1, wherein the component C polyoxyethylene sorbitol fatty acid ester has an addition molar number of oxyethylene group relative to 1 mole of sorbitol of 30 or more and 60 or less.

19. The method according to claim 1, wherein the component C polyoxyethylene sorbitol fatty acid ester has an addition molar number of oxyethylene group relative to 1 mole of sorbitol of 35 or more and 55 or less.

20. The method according to claim 1, wherein the component C polyoxyethylene sorbitol fatty acid ester is a tri-, tetra-, or penta-fatty acid ester of a sorbitol ethylene oxide adduct.

21. The method according to claim 1, wherein the component C polyoxyethylene sorbitol fatty acid ester is a tetra-fatty acid ester of a sorbitol ethylene oxide adduct.

22. The method according to claim 9, wherein the fatty acid forming the component C is oleic acid.

* * * * *